(12) United States Patent
Lea et al.

(10) Patent No.: US 12,127,894 B2
(45) Date of Patent: Oct. 29, 2024

(54) CLAMP FOR A MEDICAL DEVICE

(71) Applicant: Saban Ventures PTY Limited, Alexandria (AU)

(72) Inventors: Stephen Lea, Lane Cove (AU); Richard Jones, Hornsby Heights (AU)

(73) Assignee: Saban Ventures Pty Limited, Lane Cove West (AU)

( * ) Notice: Subject to any disclaimer, the term of this patent is extended or adjusted under 35 U.S.C. 154(b) by 826 days.

(21) Appl. No.: 17/253,323

(22) PCT Filed: Jun. 14, 2019

(86) PCT No.: PCT/AU2019/050616
§ 371 (c)(1),
(2) Date: Dec. 17, 2020

(87) PCT Pub. No.: WO2019/241833
PCT Pub. Date: Dec. 26, 2019

(65) Prior Publication Data
US 2021/0267714 A1    Sep. 2, 2021

(30) Foreign Application Priority Data
Jun. 20, 2018 (AU) ................................ 2018902195

(51) Int. Cl.
*A61L 2/26* (2006.01)
*A61B 8/00* (2006.01)
*A61B 90/57* (2016.01)

(52) U.S. Cl.
CPC ............ *A61B 90/57* (2016.02); *A61B 8/4422* (2013.01); *A61L 2/26* (2013.01); *A61L 2202/24* (2013.01)

(58) Field of Classification Search
CPC ......... A61B 90/57; A61B 8/4422; A61L 2/26; A61L 2202/24
See application file for complete search history.

(56) References Cited

U.S. PATENT DOCUMENTS

| 164,088 | A | 6/1875 | Hunter |
| 4,272,051 | A | 6/1981 | Huggins |
| 4,911,399 | A | 3/1990 | Green |
| 4,956,897 | A * | 9/1990 | Speedie ................... A43C 3/04 24/134 P |
| 5,725,158 | A | 3/1998 | Auclair |
| 9,611,875 | B2 * | 4/2017 | Likosar .................. A63C 11/02 |

(Continued)

FOREIGN PATENT DOCUMENTS

WO    WO-2011060132 A2 *  5/2011  ............... A61L 2/18

OTHER PUBLICATIONS

International Search Report and Written Opinion issued in PCT/AU2019/050616, dated Sep. 9, 2019, 9 pages.

*Primary Examiner* — Timothy C Cleveland
(74) *Attorney, Agent, or Firm* — Stinson LLP

(57) ABSTRACT

The present invention provides a clamp (10) for clamp for retaining a medical device in a medical apparatus. The clamp (10) includes a pair of opposed gripping elements (16). At least one of the gripping elements is substantially rotatably moveable to grip and apply a compressive force on a portion of the medical device when the portion it is placed between the gripping elements. The compressive force increases when the at least one of the gripping elements rotates in one direction and reduces when it rotates in an opposite direction.

20 Claims, 4 Drawing Sheets

(56) References Cited

U.S. PATENT DOCUMENTS

2008/0277545 A1 11/2008 Buchanan et al.
2010/0114041 A1 5/2010 Avery et al.
2012/0049020 A1 3/2012 Stock

* cited by examiner

CLAMP FOR A MEDICAL DEVICE

REFERENCE TO RELATED APPLICATIONS

This application is a U.S. national stage application of International Patent Application No. PCT/AU2019/050616, filed Jun. 14, 2019, which claims the benefit of Australia Patent Application No. 2018902195, filed Jun. 20, 2018, the entire disclosures of which are incorporated herein by reference.

FIELD OF INVENTION

The present invention relates to clamps and, in particular, to clamps for medical devices.

The invention has been developed as a clamp for securing a medical device within a disinfection apparatus and will be described hereinafter with reference to this application. However, it will be appreciated that the invention is not limited to this particular field of use.

BACKGROUND

The following discussion of the prior art is intended to place the invention in an appropriate technical context and enable the associated advantages to be fully understood. However, any discussion of the prior art throughout the specification should not be considered as an admission that such art is widely known or forms part of the common general knowledge in the field.

Ultrasound probes are used for a variety of intra cavity procedures including intra rectal, intra vaginal and oesophageal examination as well as surface use. These probes are constructed integrally with the power and data cord used to link the probe with a control console.

Whilst these probes do not need to be completely sterile in most cases, they do need to be subjected to disinfection. For this reason, a disinfection apparatus having a hollow cavity is typically employed. When such an apparatus is used, the probe is retained in position inside the cavity by using a resilient clamp to engage the probe's cord thereby hanging the probe in position within the cavity. Once the probe is in position, the door of the disinfection apparatus can be closed thereby sealing the cavity. Upon completion of the disinfection process, the door of the apparatus is opened, and the probe's cord can be withdrawn from the resilient clamp and the probe is withdrawn for the apparatus.

In some known disinfection apparatuses, the resilient clamp is in the form of a block of elastomeric material and more specifically, a block of silicone rubber. The block includes a pair of opposed resilient lever formations defining a slot for securing the ultrasound probe's cord therebetween. This slot expands upon insertion of the cord thereby applying a compressing gripping force onto the cord. Removal of the cord from the resilient clamp is achieved by reversing the insertion process to again expand the lever formations.

One problem with using the resilient clamp as described above is that users must take care when inserting the probe's cord into between the lever formations so that the cord is presented parallel to the slot. In this regard, this care results in additional processing time to make sure the cord is inserted correctly.

A further potential problem with these types of known resilient clamps is that they are not ideally suited to a large variation of cord diameters. More specifically, relatively small or relatively large diameter cords are not able to be ideally accommodated between the lever formations with either too small to too large compressive forces being respectively applied. In this respect, it should be appreciated that there are more than 1000 surface and intra cavity ultrasound probes presently available in the market with cord diameters ranging from 2 to 20 mm.

It is an object of the present invention to overcome or ameliorate at least one of the disadvantages of the prior art, or to provide a useful alternative.

It is an object of the present invention, in at least one preferred form, to provide a clamping device for a disinfection apparatus that can accommodate a relatively greater variation in cord diameters.

It is a further object of the present invention, in at least one preferred form, to provide a clamping device for a disinfection apparatus that is quicker to use relative to prior art clamping devices.

SUMMARY OF THE INVENTION

According to the invention, there is provided a clamp for retaining a medical device in a medical apparatus, the clamp including a pair of opposed gripping elements,
at least one of the gripping elements being substantially rotatably moveable to grip and apply a compressive force on a portion of the medical device when the portion it is placed between the gripping elements,
the compressive force increasing when the at least one of the gripping elements rotates in one direction and reducing when it rotates in an opposite direction.

In one embodiment, each of the gripping elements is substantially rotatably moveable, and wherein the compressive force is provided by each of the gripping elements.

In one embodiment, each of the gripping elements includes a gripping surface having a plurality of engagement teeth disposed thereon for gripping engagement with the portion of the medical device.

In one embodiment, each gripper element rotates about an axis of rotation, the axis of rotation being displaced from the centre of each gripper elements such that the space between corresponding gripping surfaces reduces when each of the gripper elements rotates in one direction and reduces when each gripper element is rotated in an opposite direction.

In one embodiment, each gripping element includes an outwardly extending step formation adjacent the plurality of engagement teeth for retaining the medical device between the gripping elements.

In one embodiment, each of the gripping elements includes a portion formed from a substantially resilient elastomeric material, the resilient elastomeric material providing a relatively high coefficient of friction when in contact with the portion of the medical device.

In one embodiment, the clamp includes a biasing means for rotationally biasing the gripping elements to grip the portion of the medical device when the portion it is placed between the gripping elements.

In one embodiment, the biasing means includes a coil tension spring suspended between spigots extending from each gripping element.

In one embodiment, each of the gripping elements includes tapered lead-in portion for separating the gripping elements when the portion of the medical device is pushed onto the lead-in portions.

In one embodiment, the tapered lead-in portion extends around at least half of the front surface of each gripping element.

In one embodiment, the compressive force is proportional to the weight of the medical device when the portion it is placed between the gripping elements.

In one embodiment the clamp includes a detection means for detecting the presence of the portion of the medical device between the gripping members.

In one embodiment, the detection means includes a detection bar movably mounted between a detect configuration and a non-detect configuration.

In one embodiment, the detection bar includes an elongate flag member extending therefrom, the flag member being adapted to interrupt an optical beam when the detection bar is in the non-detect configuration.

In one embodiment, the medical apparatus is a disinfection apparatus and the clamp is removably mounted to the disinfection apparatus.

In one embodiment, the portion of the medical is a cord portion of the medical device.

In one embodiment, the medical device is an ultrasound probe.

According to one aspect, the present invention provides a medical apparatus including a clamp as described above.

In one embodiment the medical apparatus is a disinfection apparatus.

Reference throughout this specification to "one embodiment", "some embodiments" or "an embodiment" means that a particular feature, structure or characteristic described in connection with the embodiment is included in at least one embodiment of the present invention. Thus, appearances of the phrases "in one embodiment", "in some embodiments" or "in an embodiment" in various places throughout this specification are not necessarily all referring to the same embodiment but may. Furthermore, the particular features, structures or characteristics may be combined in any suitable manner, as would be apparent to one of ordinary skill in the art from this disclosure, in one or more embodiments.

BRIEF DESCRIPTION OF THE DRAWINGS

Preferred embodiments of the invention will now be described, by way of example only, with reference to the accompanying drawings in which.

DETAILED DESCRIPTION OF THE PREFERRED EMBODIMENTS

Figure 1:
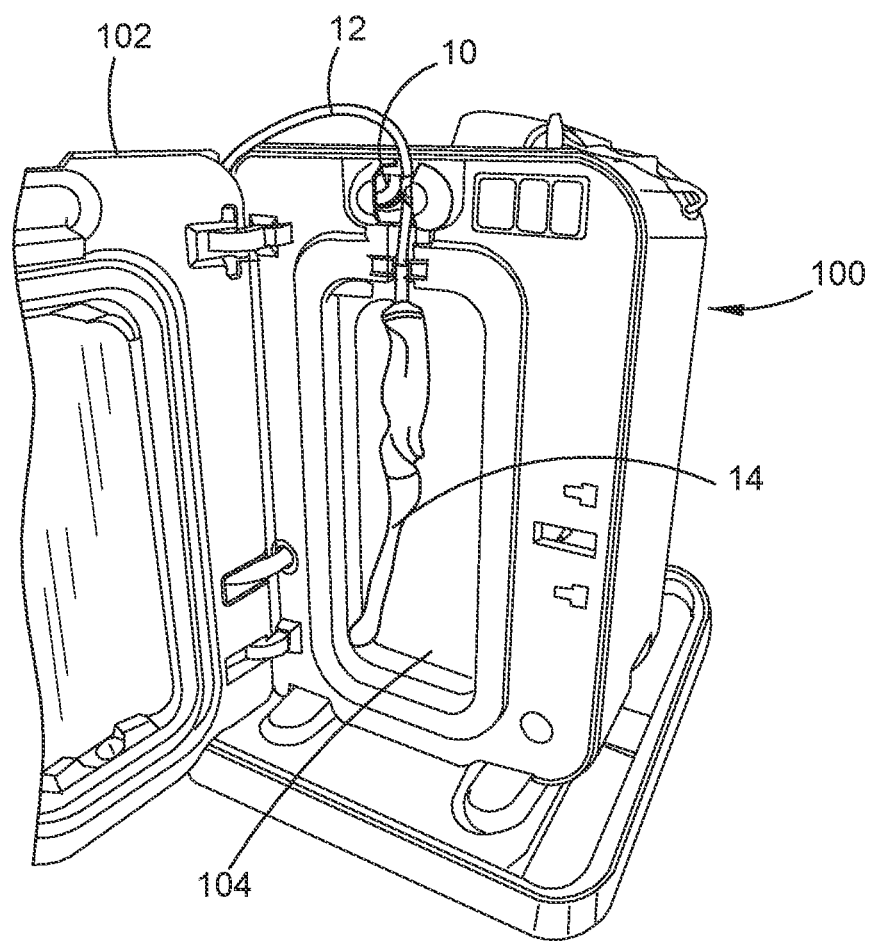
FIG. 1 is a perspective view of a disinfection apparatus showing a clamp in accordance with one embodiment of the invention.

Exemplary embodiments of the present invention will now be described in detail with reference to the accompanying drawings. In the drawings, the same elements are denoted by the same reference numerals throughout. In the following description, detailed descriptions of known functions and configurations incorporated herein have been omitted for conciseness and clarity.

Referring to FIG. 1 to initially outline the context of the invention, there is shown a disinfection apparatus 100 used for disinfecting medical devices, and in particular, for disinfecting ultrasound probes.

Ultrasound probes are used for a variety of intra cavity procedures including intra rectal, intra vaginal and oesophageal examination as well as the surface use such as prenatal inspection. These probes are constructed integrally with the power and data cord used to link the probe with a control console. Whilst the probes do not need to be completely sterile in most cases, they do need to be subjected to disinfection, usually at least high-level disinfection between each use to prevent cross-infection.

To sterilize the ultrasound probe using the illustrated apparatus, door 102 is first opened. An ultrasound probe 14 is then placed inside and secured in position. The door 102 is then closed and the disinfection process begins by a user activation. In the present case, the disinfection process involves introducing a misted disinfection agent to disperse and swirl around the ultrasound probe.

According to the invention there is provided clamp 10 for securing a medical device within a medical apparatus. In the illustrated embodiment, the clamp 10 secures the ultrasound probe 14 in position inside the disinfection apparatus 100. Clamp 10 is generally positioned at the top of the disinfection apparatus and grips onto the cord 12 of the ultrasound probe 14 to allow the probe to be suspended within a chamber 104. By suspending the probe in this way, the door 102 can be closed and the disinfection process can begin. In the illustrated embodiment, clamp 10 is removably secured to the disinfection apparatus 100 for the purposes of easy maintenance and/or replacement.

Figure 2:
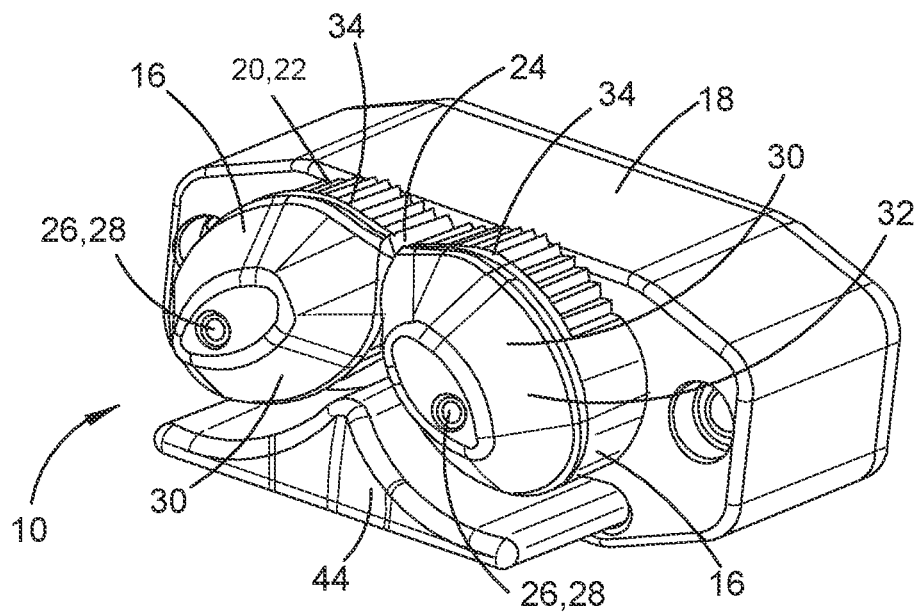
FIG. 2 is an enlarged perspective view of the clamp of FIG. 1, removed from the disinfection apparatus.

FIG. 2 shows the clamp 10 removed from the disinfection apparatus 100 to illustrate its working components. The clamp 10 includes a pair of opposed gripping elements 16. At least one of the gripping elements is rotatably movable to first grip, and then apply a compressive force onto the cord 12 of the ultrasound probe 14 once the cord is placed between the gripping elements 16. The arrangement is such that once the cord 12 is positioned between the gripping elements 16, a gripping compressive force is applied, and the probe can be then retained in the disinfection apparatus. According to the invention, the compressive force is applied by at least one gripping element 16 onto the cord 12. This force increases as the at least one gripping element rotates in one direction but will reduce when it rotates in an opposite direction.

In the illustrated embodiment, both gripping elements 16 are rotatably mounted to a housing 18 to first grip and then apply the compressive force. Similarly, the compressive force applied to the cord 12 increases when each of the gripping elements are rotated in one direction but will reduce when they are rotated in an opposite direction. As described in more detail below, due to the gripping friction between the gripping elements and the cord, once the cord is placed between the gripping elements, the downward force on the cord due to the probe's weight will rotate both gripping elements in the one direction to increase the compressive force, while upward force will reduce the compressive force.

Each gripping element includes a curved gripping surface 20 having a plurality of engagement teeth 22 disposed thereon. Further, in the illustrated embodiment, the surface of the gripper elements and the engagement teeth are formed from an elastomeric material providing a relatively high coefficient of friction when in contact with the probe's cord 12. More specifically, in the illustrated embodiment, each gripping element is formed from a rigid plastics material which is covered by a resilient elastomeric layer.

In other not shown embodiments, a protective replaceable cover for the gripper elements in the form of a thin flexible membrane may be provided to ensure that the probe cord does not come into contact with the gripper elements or any other part of the clamp. In these circumstances, it is proposed that the protective cover will be replaced between uses to prevent any chance of cross-contamination between probes.

Each gripping element 16 is generally oval-shaped having a point formation 24 at one end, which is one end of the gripping surface 20. The gripping elements 16 are rotatably connected to the housing 18 by way of axle connections 26 defining an axis of rotation 28 for each gripper element. As can be seen, each axis of rotation 28 is off-centre such that rotation of the gripper elements 16 in one direction will cause the space between corresponding gripping surfaces 20 to reduce thereby increasing the compressive force applied to the cord once it is inserted.

Each gripping element also includes a tapered lead-in portion 30 surrounding its front face 32. The tapered lead-in portions have been provided to provide a means to selectively rotate and therefore separate the gripping elements, when inserting the probe's cord 12 therebetween. The tapered lead-in portions terminate at step formations 34, which then lead to the engagement teeth 22. The step formations 34 outwardly extend above the periphery of engagement teeth 22 so that the teeth do not interfere with the insertion of the probe's cord from the front face. The step formations 34 also act to axially retain the probe's cord 12 in position.

Figure 3:
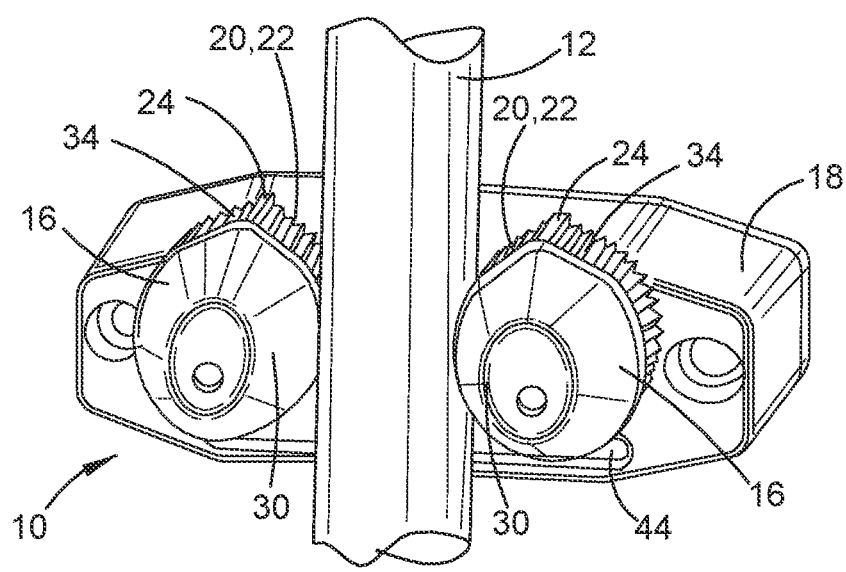
FIG. 3 is a perspective view of the clamp of FIG. 2 showing the clamp operating gripping a cord.

Referring to FIG. 3, which shows clamp 10 with the gripper elements in a separated configuration and with a cord between the gripper elements 16. The clamp has been designed such that the probe's cord 12 can be inserted by pushing it between the gripper elements 16 in a direction parallel to the rotation axis of each gripper element, from the front to the back of each gripper element 16. This pushing motion pushes the cord 12 against lead-in portions 30 thereby rotationally separating each of the gripper elements 16.

It should be appreciated that, while in the illustrated embodiment the tapered lead-in portions 30 extend around the complete front face 32 of each gripper element 16, they are only required to extend around half the front face to separate each gripper element during the insertion process. However, since two gripper elements 16 are required for each clamp 10, is more economical to produce two identical items. Therefore, the tapered lead-in portions extend around the complete front surface. This also allows the gripper elements to be advantageously interchangeable.

Figure 4:
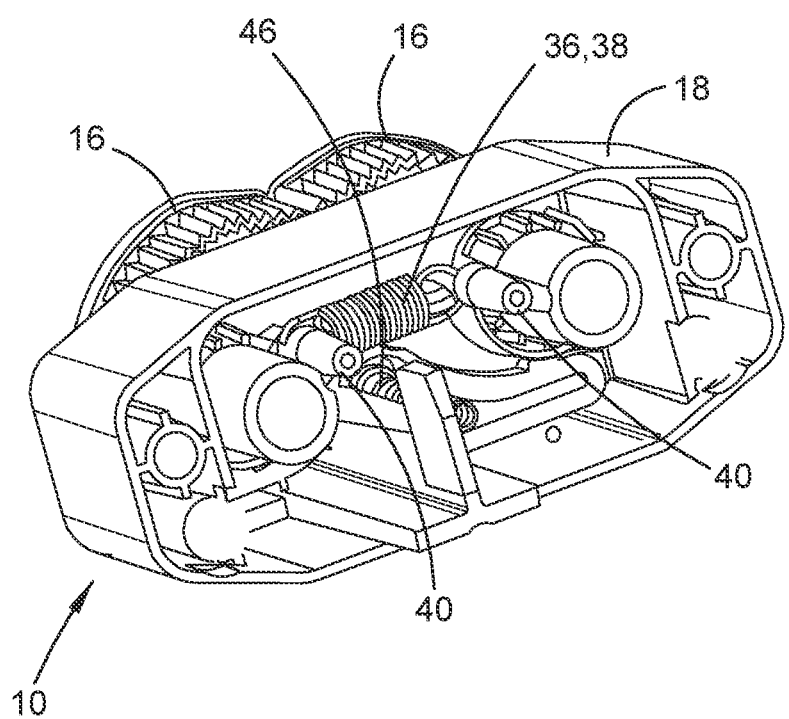
FIG. 4 is a reverse perspective view of the clamp of FIG. 2, with the rear of the housing removed.

Referring now to FIG. 4, which shows the reverse side of the clamp 10 and with the back end of the housing 18 removed. A biasing means 36 has been provided to bias the gripping elements 16 into contact and provide a preliminary compressive force onto the cord 12. The biasing means 36 includes a coil spring 38, which is suspended between spigots 40 protruding from the rear of each gripping element 16. Without departing from the scope of the invention, it should be appreciated that other forms of biasing means may be provided to bias the gripping elements into contact. These alternative biasing means may include torsion springs, plastic springs, metal leaf springs, rubber springs, magnetic attraction, or a combination of these.

In a further embodiment, the rear of each gripper element 16 includes a gearing means 42 such that the gripping elements 16 will rotate together in geared engagement.

Returning to FIG. 2, the clamp 10 of the present invention also provides a means to indicate to the disinfection apparatus 12, or outside monitoring means, that the probe's cord 12 has been completely placed between the gripping elements 16. Whilst other methods of detection are possible, in the illustrated embodiment, a detection bar 44 has been provided to achieve this task. This detection bar 44 is slidably mounted to move into the housing 18 between a rest configuration, where no cord 12 is present between the gripping elements as shown in FIG. 2, to a detect configuration where the cord is placed between the gripping elements 16 as shown in FIG. 3. In the illustrated embodiment the detection bar 44 is biased into the rest configuration by further coil spring 46 shown in FIG. 4.

Figure 5A:
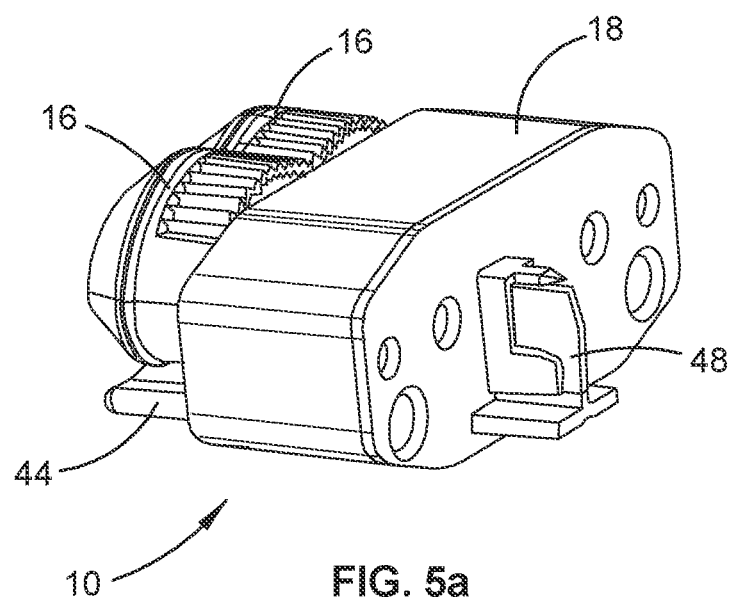
FIGS. 5a and 5b are reverse perspective views of the clamp of FIG. 2, removed from the disinfection apparatus, respectively depicting a rest configuration and a detect configuration.
Figure 5B:
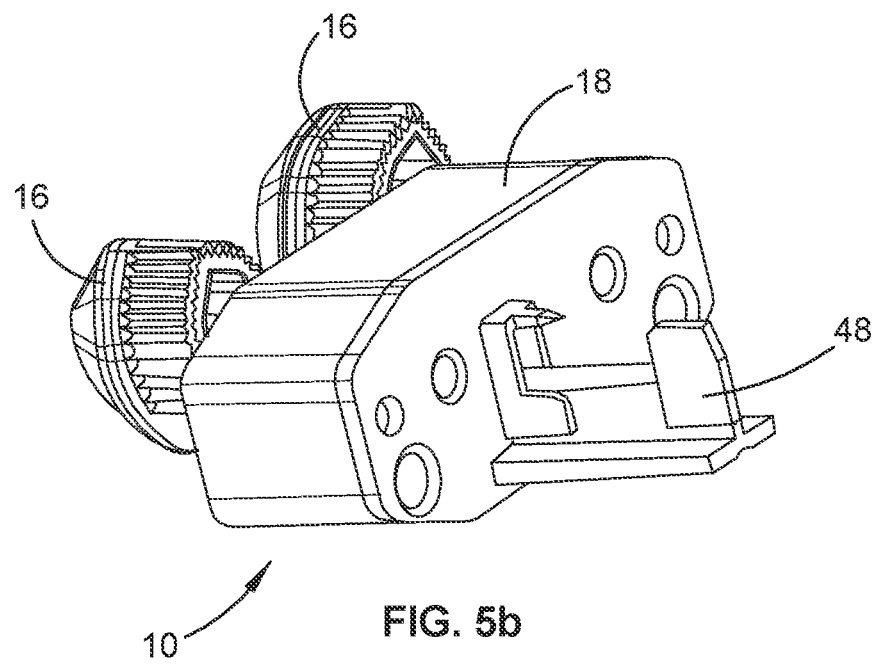

Referring now to FIGS. 5a and 5b, in one embodiment, the detection means further includes a flag member 48 extending from the rear of the detection bar 44. The flag member 48 is slidably engaged with the housing 18 and will move with the detection bar 44 from the rest configuration, as shown in FIG. 5a, to the detect configuration as shown in FIG. 5b, once the probe's cord is present the clamp. In the illustrated embodiment, the flag member 48 interrupts an optical beam produced by the disinfection apparatus in the rest configuration thereby indicating to the apparatus that no object has yet been placed between the gripping elements. Once the detection bar 44 moves to a detect configuration, the optical beam will no longer be interrupted thereby indicating to the disinfection apparatus that an object has been correctly placed between the gripping elements 16.

It is important to note that the detect configuration will only be achieved when the detect bar 44 is pushed sufficiently into the housing 18 such to indicate that the cord is substantially resting against the front of the housing 18. The disinfection process can then be allowed to proceed with the disinfection process once this condition is met. The flag member 48 is therefore configured and calibrated such that the optical beam will remain interrupted until this condition occurs. In this way, the disinfection apparatus cannot operate unless an object has been correctly placed between the gripping elements. In a preferred embodiment, a visual indicator operatively associated with the detection means will indicate when the cord 12 of the ultrasound probe 14 has been correctly installed in the clamp 10. In a further embodiment, the position of the optical beam may be moved such that the beam is interrupted only in the detect configuration. Under these circumstances, the clamp will indicate to the apparatus that the object is in position when the optical beam is interrupted.

In order to operate the clamp 10, a user simply presents the cord 12 of the ultrasound probe, or other medical device to be disinfected, to the area between the gripping elements 16. The gripping elements should be in initially contact at this point because of the biasing means. The user then simply pushes the cord 12 until it contacts the front surface of the housing 18. The pushing process will activate the lead-in portions 30 to automatically rotate and separate the gripping elements 16. The cord can then be pushed all the way to contact the front surface of the housing 18. At the same time, the lower portion of the cord pushes the detection bar 44 to be flush with the front surface of housing 18 thereby indicating to the disinfection apparatus that the cord 12 is correctly in position.

Due again to the biasing means, the gripping elements will automatically rotate and grip the sides of the cord once it has reached this position to provide an initial compressive force and positive frictional contact between the teeth 22 and the cord 12. The downward force on the cord due to the weight of the probe 14 will then act to rotate the gripping elements 16 closer together to apply the primary compressive force onto the cord. In this respect, it will be appreciated that heavier ultrasound probes will be equally held in position as they will increase the compressive force on their cords.

In a similar vein, an upward force on the cord will act to rotate the gripping elements in an opposite direction to thereby reduce the compressive force on the cord. Therefore, to reposition the ultrasound probe from the apparatus, a user simply pulls upwardly to adjust the height of the probe in the apparatus.

To withdraw the ultrasonic probe from the apparatus once the disinfection process is complete, the user applies a combined upward and outward force to the cord in an opposite direction to the insertion force. Advantageously, this process is quickly and easily completed without the user having to be concerned about correctly orientating the cord.

Advantageously, the clamp 10 of the present invention allows a greater range of cord diameters to be accommodated than prior art clamps. Due to the amount of spring load provided by the biasing means 36, the degree of frictional load or rubbing load applied on the cord of the probe as it is inserted into the clamp is minimised thereby lessening the possibility of damage to the cord over repeated uses. The clamp can also accommodate a varied different sized ultrasound probes as the compressive load applied to the cord will be proportional to the weight of the probe itself.

The invention also advantageously allows for quicker insertion and withdrawal of ultrasound probes from the disinfection apparatus relative to prior art clamps due to the user not being concerned with correct alignment of the cord at these times.

It should be appreciated that whilst the invention has been described in the context of a clamp for securing a medical device within a disinfection apparatus, the clamp may be used with other medical devices without departing from the scope of the invention.

It should be appreciated that in the above description of exemplary embodiments of the invention, various features of the invention are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

While there has been described what are believed to be the preferred embodiments of the invention, those skilled in the art will recognize that other and further modifications may be made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

The invention claimed is:

1. A clamp for retaining a medical device in a medical apparatus, said clamp including a pair of opposed gripping elements,
   at least one of said gripping elements being substantially rotatably moveable to grip and apply a compressive force on a portion of said medical device when said portion is placed between said gripping elements,
   said compressive force increasing when said at least one of said gripping elements rotates in one direction and reducing when it rotates in an opposite direction,
   wherein each gripping element includes a tapered lead-in portion for separating said gripping elements when said portion of said medical device is pushed onto said tapered lead-in portions, said tapered lead-in portion forming a front face of each gripping element, and
   wherein each gripping element includes a gripping surface for gripping engagement with said portion of said medical device, and each gripping element includes a step formation between said front face and said gripping surface to prevent interference of said gripping surface with insertion of said portion of said medical device.

2. A clamp according to claim 1, wherein said front face includes a central portion, and wherein said tapered lead-in portion is tapered from said central portion and to said step formation.

3. A clamp according to claim 1, wherein said gripping surface includes a plurality of engagement teeth, and wherein said step formation extends adjacent to said plurality of engagement teeth for axially retaining said medical device between said gripping elements.

4. A clamp according to claim 3, wherein said step formation extends outwardly adjacent to and above the periphery of said plurality of engagement teeth.

5. A clamp according to claim 1, wherein said tapered lead-in portion extends from and is positioned around a central portion of each gripping element, such that each gripping element is interchangeable with the other.

6. A clamp according to claim 1, wherein each of said gripping elements is rotatably moveable, and wherein said compressive force is provided by each of said gripping elements.

7. A clamp according to claim 6, wherein each gripping element rotates about an axis of rotation, said axis of rotation being displaced from the center of each gripping element such that the space between corresponding gripping surfaces reduces when each of said gripping elements rotates in one direction and increases when each gripping element is rotated in an opposite direction.

8. A clamp according to claim 1, wherein each of said gripping elements includes a portion formed from a substantially resilient elastomeric material, said resilient elastomeric material providing a relatively high coefficient of friction when in contact with said portion of said medical device.

9. A clamp according to claim 1, including a coil tension spring suspended between spigots extending from each gripping element for rotationally biasing said gripping elements to grip said portion of said medical device when said portion is placed between said gripping elements.

10. A clamp according to claim 1, wherein said front face includes a central portion, and wherein said tapered lead-in portion extends from and at least half way around said central portion of each gripping element.

11. A clamp according to claim 1, wherein said compressive force is proportional to the weight of said medical device when said portion is placed between said gripping elements.

12. A clamp according to claim 1 including a detection bar for detecting the presence of said portion of said medical device between said gripping elements.

13. A clamp according to claim 12, wherein said detection bar is movably mounted for movement between a detect configuration and a non-detect configuration.

14. A clamp according to claim 13, wherein said detection bar includes an elongate flag member extending therefrom, said flag member being adapted to interrupt an optical beam when said detection bar is in said non-detect configuration.

15. A clamp according to claim 1, wherein said medical apparatus is a disinfection apparatus and said clamp is removably mounted to said disinfection apparatus.

16. A clamp according to claim 1, wherein said portion of said medical device is a cord portion of said medical device.

17. A clamp according to claim 1, wherein said medical device is an ultrasound probe.

18. A medical apparatus including a clamp according to claim 1.

19. A medical apparatus according to claim 18, wherein said medical apparatus is a disinfection apparatus.

20. A clamp according to claim 10, wherein said tapered lead-in portion extends from and completely around said central portion of each gripping element.

* * * * *